US010285931B2

(12) United States Patent
Kerl et al.

(10) Patent No.: US 10,285,931 B2
(45) Date of Patent: May 14, 2019

(54) OXIDATIVE HAIR DYE WITH OPTIMIZED LIFT PERFORMANCE

(71) Applicant: Henkel AG & Co. KGaA, Duesseldorf (DE)

(72) Inventors: Sylvia Kerl, Hamburg (DE); Katharina Krause, Hamburg (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 3 days.

(21) Appl. No.: 15/691,184

(22) Filed: Aug. 30, 2017

(65) Prior Publication Data

US 2018/0064634 A1 Mar. 8, 2018

(30) Foreign Application Priority Data

Sep. 6, 2016 (DE) .................. 10 2016 216 866

(51) Int. Cl.

| *A61Q 5/10* | (2006.01) |
|---|---|
| *A61K 8/9789* | (2017.01) |
| *A61K 8/22* | (2006.01) |
| *A61K 8/34* | (2006.01) |
| *A61K 8/41* | (2006.01) |
| *A61K 8/46* | (2006.01) |
| *A61K 8/49* | (2006.01) |
| *A61K 8/92* | (2006.01) |

(52) U.S. Cl.

CPC ............. *A61K 8/9789* (2017.08); *A61K 8/22* (2013.01); *A61K 8/342* (2013.01); *A61K 8/347* (2013.01); *A61K 8/41* (2013.01); *A61K 8/411* (2013.01); *A61K 8/415* (2013.01); *A61K 8/463* (2013.01); *A61K 8/494* (2013.01); *A61K 8/4946* (2013.01); *A61K 8/922* (2013.01); *A61Q 5/10* (2013.01)

(58) Field of Classification Search

CPC .......... A61Q 5/10; A61K 8/922; A61K 8/463; A61K 8/415; A61K 8/411; A61K 8/41; A61K 8/347; A61K 8/342; A61K 8/22

See application file for complete search history.

(56) References Cited

U.S. PATENT DOCUMENTS

| 8,293,291 B2 | 10/2012 | Smith |
| 2012/0225141 A1 | 9/2012 | Bouez et al. |
| 2015/0056255 A1* | 2/2015 | Ragot ................. A23L 2/395 |
| | | 424/401 |
| 2015/0056310 A1 | 2/2015 | Cenizo et al. |

FOREIGN PATENT DOCUMENTS

| CN | 105853314 A | 8/2016 |
| DE | 19756454 C1 | 6/1999 |
| DE | 102013213027 A1 | 4/2014 |
| JP | 2003081850 A | 9/2001 |

OTHER PUBLICATIONS

Intellectual Property Office, Search Report under Section 17(5) for United Kingdom Patent Application No. GB1714186.2 dated Apr. 23, 2018.

* cited by examiner

*Primary Examiner* — Eisa B Elhilo

(74) *Attorney, Agent, or Firm* — Lorenz & Kopf, LLP

(57) ABSTRACT

The subject matter of the present disclosure is an oxidative dye for oxidative color change of keratinic fibers, in particular human hair which contains, in a cosmetically suitable vehicle, at least one alkalizing agent, at least one oxidative dye precursor of the developer type and at least one oxidative dye precursor of the coupler type, at least one extract of Quassia amara and, based on the weight of the oxidative dye, from about 0 to less than about 0.1 wt % peroxide compounds.

18 Claims, No Drawings

OXIDATIVE HAIR DYE WITH OPTIMIZED LIFT PERFORMANCE

CROSS-REFERENCE TO RELATED APPLICATION

This application claims priority to German Patent Application No. 102016216866.5, filed Sep. 6, 2016, which is incorporated herein by reference in its entirety.

TECHNICAL FIELD

The present disclosure relates to a hair dye for oxidative dyeing of hair, said hair dye having optimized lift performance as well as a method for oxidative hair dyeing using an oxidative hair dye having optimized lift performance.

BACKGROUND

So-called oxidative dyes are used for permanent intense dyeings with appropriate fastness properties. Oxidative dyes usually include two components, one component usually containing oxidative dye precursors, so-called developer components and coupler components. The developer components form the actual coloring substances under the influence of oxidizing agents, in particular hydrogen peroxide, which are added to the first component shortly before application to the hair, or under the influence of atmospheric oxygen or with coupling to one or more coupler components. The developer components generally include primary aromatic amines with an additional free or substituted hydroxyl group or amino group in para- or ortho-position, also including diaminopyridine derivatives, heterocyclic hydrazones, 4-amino¬pyrazolone derivatives and 2,4,5,6-tetraaminopyrimidine and derivatives thereof. Suitable coupler components usually include m-phenylenediamine derivatives, naphthols, resorcinol and resorcinol derivatives, pyrazolones, m-aminophenols and substituted pyridine derivatives. The oxidative dyes have excellent and long-lasting dyeing results.

Conventional oxidative dyes have a more alkaline pH which is definitely above 9.0 and is adjusted with alkalizing agents such as alkanolamines, ammonia or inorganic bases to stabilize the dye precursors during storage and to accelerate the reaction during oxidative application. Ammonia in particular gives good dyeing results but also has disadvantages for the user due to its odor and potential for irritation of skin and mucous membranes. The alkalizing agent causes swelling of keratinic fibers so that the dye precursors can penetrate well into the hair. However, the damaging effect of the oxidizing agent on the hair structure is also increased by the alkaline pH.

Therefore, special efforts have been devoted to the development of high-performance oxidative dyes containing one or more substances that essentially have no oxidizing effect but can enhance the effect of the oxidizing agent, in order to reduce the concentration thereof, while at the same time manifesting results with regard to lightening and dyeing. Then the reduction in oxidizing agent concentration may be associated with reduced damage to hair.

Prior Art. The use of Quassia amara extracts in cosmetic compositions was already known. For example, JP 2003 081850 A, WO 2007/048985, U.S. Pat. No. 8,293,291 and US 20150056310 A1 describe the use of Quassia amara extracts as wrinkle-reducing active ingredients to reduce facial lines or to strengthen the extracellular matrix (ECM) of facial skin. DE 102013213027A1 discloses the use of Quassia amara extracts to improve hair structure and promote hair growth.

BRIEF SUMMARY

Oxidative dyes are provided herein. In an embodiment, an oxidative dye is provided for oxidative color change of keratinic fibers. The oxidative dye includes, in a cosmetically suitable vehicle, at least one alkalizing agent, at least one oxidative dye precursor of the developer type and at least one oxidative dye precursor of the coupler type, at least one extract of Quassia amara and from about 0 to less than about 0.1 wt % of peroxide compounds, based on the weight of the oxidative dye.

In another embodiment, an oxidative dye is provided for oxidative color change of keratinic fibers. The oxidative dye includes, in a cosmetically suitable vehicle, at least one alkalizing agent, at least one oxidative dye precursor of the developer type and at least one oxidative dye precursor of the coupler type, at least one extract of Quassia amara, from about 0 to less than about 0.1 wt % of peroxide compounds, based on the weight of the oxidative dye, at least one cosmetic oil, at least one surfactant, and at least one linear saturated alkanol with from 12 to 30 carbon atoms. The at least one extract of Quassia amara amounts to a total of from about 0.15 to about 0.5 wt %, based on the weight of the oxidative dye. The at least one cosmetic oil is included in a total amount of from about 2 to about 10 wt %, based on the weight of the oxidative dye. The at least one surfactant is included in a total amount of from about 1 to about 10 wt %, based on the weight of the oxidative dye. The at least one linear saturated alkanol with from 12 to 30 carbon atoms is included in a total amount of from about 3 to about 10 wt %, based on the weight of the oxidative dye.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

It has now been found that a dye containing at least one extract of Quassia amara can improve the lightening effect of an oxidative dye treatment. Using the contemplated dyes, a stronger lightening effect is achieved than with similar dyes containing no Quassia amara extract.

In a first embodiment, the subject matter of the present disclosure is an oxidative dye for oxidatively changing the color of keratinic fibers, in particular human hair, said hair dye containing at least one alkalizing agent, at least one oxidative dye precursor of the developer type and at least one oxidative dye precursor of the coupler type plus at least one extract of Quassia amara and, based on the weight of the oxidative dye, from about 0 to about <0.1 wt % peroxide compounds in a suitable cosmetic vehicle. Oxidative dyes that are preferred as contemplated herein contain a total of from about 0.01 to about 3 wt %, preferably from about 0.05 to about 1.5 wt %, especially preferably from about 0.1 to about 1 wt %, extremely preferably from about 0.15 to about 0.5 wt % of at least one extract of Quassia amara, each based on the weight of the oxidative dye.

Quassia amara is a tropical bush from the Simaroubaceae family that grows to a height of from about 2 to about 5 meters. Originally found in Guyana, today the plant grows mainly in Central and South America, where it is also known as Surinam quassia or amargo and is often confused with Jamaican quassia.

An extract in the sense of the present application is a substance or substance mixture obtained by extraction and partial or complete evaporation of the extraction solution. A differentiation is made according to the property of the dry extracts, i.e., extracts evaporated until they are dry, liquid extracts, i.e., extracts prepared with solvents, so that one part of the herbal preparation yields at most two parts of liquid extract, viscous extracts, i.e., thick extracts, i.e., extracts in which a portion of the solvent is evaporated.

The extracts used as contemplated herein are preferably obtained from wood, especially preferably from the bark-free wood of Quassia amara.

The extracts used as contemplated herein can be prepared with water as well as polar or apolar organic solvents and mixtures thereof in a manner with which those skilled in the art are familiar. The extracts used as contemplated herein are obtained by extraction preferably with water or mixtures of water and at least one organic solvent. Suitable organic solvents preferably include ketones (e.g., acetone), ethers, esters, alcohols or halogenated hydrocarbons. Especially preferred extracting agents include water and aqueous-alcohols mixtures. Of the alcohols, $C_1$ to $C_6$ alcohols such as ethanol and isopropanol are preferred. Especially preferred extracting agents include water, ethanol, 2-propanol, 1,2-propylene glycol, 1,3-butylene glycol, most especially preferably water, ethanol, 2-propanol and 1,2-propylene glycol as well as mixtures thereof, e.g., a mixture of 1,2-propylene glycol and water in a 4:1 ratio.

Water is a preferred extracting agent for extracting the extracts used as contemplated herein. However, water itself is not a Quassia amara extract as contemplated herein.

The extracts of Quassia amara used as contemplated herein, preferably from bark-free wood, can be obtained by known production processes using polar solvents such as water, methanol, ethanol, acetone, etc. and mixtures thereof, as described above, at temperatures of from about 15° C. to about 100° C., preferably at a temperature of from about 25° C. to about 90° C. while mixing either weakly or very strongly and thoroughly for from about 10 minutes up to about 24 hours under pressures of from about 1 bar to about 200 bar.

To increase the concentration of the components that are responsible for the desired effect, additional concentration steps may also be carried out, such as liquid-liquid distribution with 1-butanol/water or ethyl acetate/water, for example, or adsorption-desorption on ion exchangers, LH20, HP20 and other resins or chromatographic separation on RP18, silica gel, etc. If further processing to yield dry extracts is desired, this is performed according to known methods by drawing off the solvent at an elevated temperature and/or reduced pressure.

In another preferred embodiment as contemplated herein, the extract that has been concentrated as described above can be preserved and/or hydrophobized by adding at least one polar solvent selected from 1,2-propanediol, glycerol, 1,3-butylene glycol, 1,2-pentanediol and 1,6-hexanediol as well as mixtures thereof, in particular by adding 1,3-butylene glycol and 1,2-pentanediol. Such extracts contain a total amount of at least one polar solvent selected from 1,2-propanediol, glycerol, 1,3-butylene glycol, 1,2-pentanediol and 1,6-hexanediol as well as mixtures thereof, from about 5 to about 50 wt %, preferably from about 10 to about 30 wt %, especially preferably from about 15 to about 25 wt %, based on the weight of the extract.

Depending on the choice of the extracting agent, it may be preferable to stabilize the extract by adding a solubilizer. Suitable solubilizers include, for example, ethoxylation products of optionally hardened vegetable oils and animal oils. Preferred solubilizers include ethoxylated mono-, di- and triglycerides of $C_{8-22}$ fatty acids with from about 4 to about 50 ethylene oxide units, e.g., hydrogenated ethoxylated castor oil, polyoxyethylene glycerol monolaurate, olive oil ethoxylate, polyoxyethylene glycol caprylic/capric acid glycerides and polyoxyethylene glycol coco fatty acid glycerides.

The dry weight of the extract, i.e., the weight of the extracted Quassia amara ingredients, depends on the molecular weight and the solubility of the ingredients extracted from Quassia amara, in particular bark-free Quassia amara wood. As a rule, the dry weight amounts to from about 1 to about 80 wt %, based on the weight of the extract. The dry weight preferably amounts to from about 5 to about 50 wt % and especially preferably from about 7 to about 25 wt %. Extracts of Quassia amara, in particular from bark-free Quassia amara wood, that are especially preferred for use as contemplated herein have a dry weight of from about 5 to about 50 wt %, especially preferably from about 7.5 to about 30 wt %, based on the weight of the extract.

Extremely preferred as contemplated herein are extracts that are obtained from bark-free Quassia amara wood with water and have a dry weight of from about 7 to about 25 wt %, based on the weight of the extract, containing 1,3-butylene glycol and 1,2-pentanediol—preferably in a total amount of from about 5 to about 50 wt %, preferably from about 10 to about 30 wt %, especially preferably from about 15 to about 25 wt %, based on the weight of the extract.

The oxidative dye as contemplated herein may be formulated as a water-based emulsion or as a spray, cream, gel, lotion, paste or shampoo.

Oxidative dyeing processes on keratin fibers usually take place in an alkaline medium. To protect the keratin fibers and the skin as much as possible, however, it is not desirable for the pH to be too high. It is therefore preferable if the pH of the oxidative dye preferred as contemplated herein is in the range of from about 7 to about 11, in particular in the range of from about 8 to about 10.5. The pH levels in the sense of the present disclosure were measured at a temperature of 22° C.

The alkalizing agents that can be used to adjust the preferred pH as contemplated herein may be selected from the group comprising ammonia, basic amino acids, alkali hydroxides, alkanolamines, alkali metal metasilicates, alkali phosphates and alkali hydrogen phosphates. Preferred alkali metal ions includes lithium, sodium, potassium and in particular sodium or potassium.

The basic amino acids that can be used as alkalizing agents as contemplated herein are preferably selected from the group comprising L-arginine, D-arginine, D,L-arginine, L-lysine, D-lysine, D,L-lysine, especially preferably L-arginine, D-arginine, D,L-arginine. The alkali hydroxides that can be used as alkalizing agents are preferably selected from the group comprised of sodium hydroxide and potassium hydroxide.

The alkanolamines that can be used as alkalizing agents are preferably selected from primary amines with a $C_2$-$C_6$ alkyl base substance having at least one hydroxyl group. Especially preferred alkanolamines are selected from the group formed by 2-amino-1-ethanol (monoethanolamine), 3-amino-1-propanol, 4-amino-1-butanol, 5-amino-1-pentanol, 1-amino-2-propanol, 1-amino-2-butanol, 1-amino-2-pentanol, 1-amino-3-pentanol, 1-amino-4-pentanol, 3-amino-2-methyl-1-propanol, 1-amino-2-methyl-2-propanol, 3-aminopropane-1,2-diol, 2-amino-2-methylpropane-1,3-diol. Alkanolamines that are most especially preferred as contemplated herein are selected from the group comprising 2-amino-1-ethanol, 2-amino-2-methyl-1-propanol and 2-amino-2-methylpropane-1,3-diol.

The oxidative dye as contemplated herein optionally contains, based on its weight, at least one cosmetic oil in a total amount of from about 0.1 to about 80 wt %, preferably from about 0.2 to about 60 wt %, especially preferably from about 1 to about 30 wt %, extremely preferably from about 2 to about 10 wt %. The cosmetic oil is liquid under normal conditions (20° C., 1013.25 mbar). Essential oils and perfume oils and/or fragrances are not counted with the cosmetic oils. The cosmetic oils that are liquid under normal conditions are not miscible with water. Essential oils are understood as contemplated herein to be mixtures of volatile components prepared by steam distillation from plant-based raw materials such as citrus oils. When speaking of a cosmetic oil in the present patent application, it should always be understood to refer to a cosmetic oil that is not a fragrance and is not an essential oil, is liquid under normal conditions and is not miscible with water.

The definition of a fragrance in the sense of the present patent application corresponds to the definition customarily used by those skilled in the art as can be found in the Römpp Chemical Lexicon, December 2007 edition, according to which a fragrance is a chemical compound with an odor and/or taste stimulating the receptors of the hair cells of the olfactory system (adequate stimulus). The required physical and chemical properties include a low molecular weight of max. 300 g/mol, a high vapor pressure, a minimal water solubility and a high lipid solubility as well as a weak polarity and the presence of at least one osmophoric group in the molecule. To differentiate volatile low molecular substances, which are not conventionally regarded as fragrances (including in the sense of the present patent application), but instead are considered and used primarily as solvents, such as ethanol, propanol, isopropanol and acetone, from the fragrances according to the present disclosure, the fragrances as contemplated herein have a molecular weight of from about 74 to about 300 g/mol, contain at least one osmophoric group in the molecule and have an odor and/or taste, i.e., they stimulate the receptors of the hair cells of the olfactory system.

Especially preferred oils as contemplated herein are selected from the esters of the linear or branched, saturated or unsaturated fatty alcohols with from 2-30 carbon atoms, with linear or branched, saturated or unsaturated fatty acids with from 2-30 carbon atoms, which may be hydroxylated. These include cetyl-2-ethylhexanoate, 2-hexyldecylstearate, 2-hexyldecyl laurate, isodecyl neopentanoate, isononyl isononanoate, 2-ethylhexyl palmitate and 2-ethylhexyl stearate. Also preferred are isopropyl myristate, isopropyl palmitate, isopropyl stearate, isopropyl isostearate, isopropyl oleate, isooctyl stearate, isononyl stearate, isocetyl stearate, isononyl isononanoate, isotridecyl isononanoate, cetearyl isononanoate, 2-ethylhexyl laurate, 2-ethylhexyl isostearate, 2-ethylhexyl cocoate, 2-octyldodecyl palmitate, butyloctanoic acid 2-butyl octanoate, diisotridecyl acetate, n-butyl stearate, n-hexyl laurate, n-decyl oleate, oleyl oleate, oleyl erucate, erucyl oleate, erucyl erucate, ethylene glycol dioleate and ethylene glycol dipalmitate.

Additional preferred oils as contemplated herein are selected from natural and synthetic hydrocarbons, especially preferably from mineral oils, paraffin oils, $C_{18}$-$C_{30}$ isoparaffins, in particular isoeicosane, polyisobutenes and polydecenes, which are available under the brand name Emery® 3004, 3006, 3010, for example, or under the brand name Ethylflo® from Albemarle or Nexbase® 2004G from Nestle or also selected from $C_8$-$C_{16}$ isoparaffins, in particular isodecane, isododecane, isotetradecane and isohexadecane as well as mixtures thereof and also 1,3-di-(2-ethylhexyl)cyclohexane.

Additional preferred oils as contemplated herein are selected from the benzoic acid esters of linear or branched $C_{8-22}$ alkanols. Especially preferred are benzoic acid $C_{12}$-$C_{15}$ alkyl esters, benzoic acid isostearyl esters, ethyl hexyl benzoate and benzoic acid octyl dodecyl esters.

Additional preferred oils as contemplated herein are selected from fatty alcohols with 6-30 carbon atoms, which may be unsaturated or branched and unsaturated or branched and saturated. The branched alcohols are frequently also referred to as Guerbet alcohols because they can be obtained by the Guerbet reaction. Preferred alcohols include 2-hexyldecanol, 2-octyldodecanol, 2-ethylhexyl alcohol and isostearyl alcohol.

Additional preferred oils are selected from mixtures of Guerbet alcohols and Guerbet alcohol esters, e.g., mixtures of 2-hexyldecanol and 2-hexyldecyl laurate.

Additional preferred cosmetic oils as contemplated herein are selected from the triglycerides (=triple esters of glycerol) of linear or branched, saturated or unsaturated optionally hydroxylated $C_{8-30}$ fatty acids. The use of natural oils may be especially preferred, for example, amaranth seed oil, apricot kernel oil, argan oil, avocado oil, babassu oil, cottonseed oil, borage seed oil, camelina oil, thistle oil, peanut oil, pomegranate seed oil, grapefruit seed oil, hemp oil, hazel nut oil, elderberry seed oil, current seed oil, jojoba oil, linseed oil, macadamia nut oil, corn germ oil, almond oil, marula oil, evening primrose oil, olive oil, palm oil, palm kernel oil, Brazil nut oil, pecan oil, peach kernel oil, rapeseed oil, castor oil, sea buckthorn fruit oil, sea buckthorn seed oil, sesame oil, soy oil, sunflower oil, grapeseed oil, walnut oil, wild rose oil, wheat germ oil and the liquid fractions of coconut oil and the like. However, synthetic triglyceride oils in particular capric/caprylic triglycerides, for example, the commercial products Myritol® 318, Myritol® 331 (BASF) or Miglyol® 812 (Hüls) with unbranched fatty acid radicals and glyceryl triisostearol with branched fatty acid radicals are also preferred.

Additional particularly preferred cosmetic oils as contemplated herein are selected from the dicarboxylic acid esters of linear or branched $C_2$-$C_{10}$ alkanols, in particular diisopropyl adipate, di-n-butyl adipate, di-(2-ethylhexyl) adipate, dioctyl adipate, diethyl/di-n-butyl/dioctyl sebacate, diisopropyl sebacate, dioctyl malate, dioctyl maleate, dicaprylyl maleate, diisooctyl succinate, di-2-ethylhexyl succinate and di-(2-hexyldecyl) succinate.

Additional preferred cosmetic oils as contemplated herein are selected from the addition products of from 1 to 5 propylene oxide units onto monovalent or polyvalent $C_{8-22}$ alkanols such as octanol, decanol, decanediol, lauryl alcohol, myristyl alcohol and stearyl alcohol, e.g., PPG-2-myristyl ether and PPG-3-myristyl ether. Additional preferred cosmetic oils as contemplated herein are selected from the addition products of at least six ethylene oxide units and/or propylene oxide units onto monovalent or polyvalent $C_{3-22}$ alkanols such as glycerol, butanol, butanediol, myristyl alcohol and stearyl alcohol which may be esterified if desired, e.g., PPG-14-butyl ether, PPG-9-butyl ether, PPG-10-butanediol, PPG-15-stearyl ether and glycerth-7-diisononanoate.

Additional preferred cosmetic oils as contemplated herein are selected from the $C_8$-$C_{22}$ fatty alcohol esters of monovalent or polyvalent $C_2$-$C_7$ hydroxycarboxylic acids, in particular the esters of glycolic acid, lactic acid, malic acid, tartaric acid, citric acid and salicylic acid.

Additional preferred cosmetic oils as contemplated herein are selected from the symmetrical, asymmetrical or cyclic esters of carbonic acids with $C_{3-22}$ alkanols, $C_{3-22}$ alkanediols or $C_{3-22}$ alkanetriols, e.g., dicaprylyl carbonate or the esters according to the teaching of DE 19756454 A1, in particular glycerol carbonate.

Additional cosmetic oils that may be preferred as contemplated herein are selected from the esters of dimers of unsaturated $C_{12}$-$C_{22}$ fatty acids (dimer fatty acids) with monovalent linear, branched or cyclic $C_2$-$C_{18}$ alkanols or with polyvalent linear or branched $C_2$-$C_6$ alkanols.

Additional cosmetic oils that are suitable as contemplated herein are selected from the silicone oils, which include, for example, dialkyl siloxanes and alkylaryl siloxanes, such as, for example, cyclopentasiloxane, cyclohexasiloxane, dimethylpolysiloxane and methyl phenyl polysiloxane, but also hexamethyl disiloxane, octamethyl trisiloxane and decamethyl tetrasiloxane. Volatile silicone oils that may be cyclic, such as octamethylcyclotetrasiloxane, decamethylcyclopentasiloxane and dodecamethylcyclohexasiloxane as well as mixtures thereof, such as those available in the commercial products DC 244, 245, 344 and 345 from Dow Corning, may also be preferred. Also suitable are volatile linear silicone oils, in particular hexamethyldisiloxane ($L_2$), octamethyltrisiloxane ($L_3$), decamethyltetrasiloxane ($L_4$) as well as any binary and ternary mixtures of $L_2$, $L_3$ and/or $L_4$, preferably mixtures such as those contained in the commercial products DC 2-1184, Dow Corning® 200 (0.65 cSt) and Dow Corning® 200 (1.5 cSt) from Dow Corning. Preferred nonvolatile silicone oils are selected from higher molecular linear dimethylpolysiloxanes, which are available commercially under the brand names Dow Corning® 190 and Dow Corning® 200 fluid with kinematic viscosities (25° C.) in the range of from about 5 to about 100 cSt, preferably from about 5 to about 50 cSt, or also from about 5 to about 10 cSt, and dimethylpolysiloxane with a kinematic viscosity (25° C.) of approximately 350 cSt.

It may be extremely preferred as contemplated herein to use mixtures of the aforementioned oils.

Preferred dyes as contemplated herein are exemplified in that the cosmetic oil is selected from natural and synthetic hydrocarbons, especially preferably from paraffin oils, $C_{18}$-$C_{30}$ isoparaffins, in particular isoeicosane, polyisobutenes and polydecenes, $C_8$-$C_{16}$ isoparaffins as well as 1,3-di-(2-ethylhexyl)cyclohexane; the benzoic acid esters of linear or branched $C_{8-22}$ alkanols; fatty alcohols with from 6 to 30 carbon atoms, which are unsaturated or branched and unsaturated or branched and saturated; triglycerides of linear or branched, saturated or unsaturated, optionally hydroxylated $C_{8-30}$ fatty acids in particular natural oils; the dicarboxylic acid esters of linear or branched $C_2$-$C_{10}$ alkanols; the esters of linear or branched, saturated or unsaturated fatty alcohols with from 2-30 carbon atoms with linear or branched, saturated or unsaturated fatty acids with from 2-30 carbon atoms, which may be hydroxylated; the addition products of from 1 to 5 propylene oxide units onto monovalent or polyvalent $C_{8-22}$ alkanols; the addition products of at least 6 ethylene oxide units and/or propylene oxide units onto monovalent or polyvalent $C_{3-22}$ alkanols; the $C_8$-$C_{22}$ fatty alcohol esters of monovalent or polyvalent $C_2$-$C_7$ hydroxycarboxylic acids; the symmetrical, asymmetrical or cyclic esters of carboxylic acid with $C_{3-22}$ alkanols, $C_{3-22}$ alkanediols or $C_{3-22}$ alkanetriols; the esters of dimers of unsaturated $C_{12}$-$C_{22}$ fatty acids (dimer fatty acids) with monovalent linear, branched or cyclic $C_2$-$C_{18}$ alkanols or with polyvalent linear or branched $C_2$-$C_6$ alkanols; silicone oils as well as mixtures of the aforementioned substances.

Additional preferred oxidative dyes as contemplated herein contain at least one surfactant or one emulsifier.

Surfactants and emulsifiers in the sense of the present disclosure are amphiphilic (bifunctional) compounds including at least one hydrophobic molecule part and at least one hydrophilic molecule part. The hydrophobic radical is preferably a hydrocarbon chain with from 8-28 carbon atoms, which may be saturated or unsaturated, linear or branched. This $C_8$-$C_{28}$ alkyl chain is especially preferably linear. The basic properties of the surfactants and emulsifiers include the oriented absorption onto interfaces as well as the aggregation to form micelles and the development of lyotrophic phases.

In the choice of suitable surfactants as contemplated herein, it may be preferable to use a mixture of surfactants in order to optimize the stability of the oxidative dye as contemplated herein.

Preferred surfactants and emulsifiers are selected from anionic, cationic, zwitterionic, amphoteric and nonionic surfactants and emulsifiers. These substances are described in detail below.

Preferred oxidative dyes as contemplated herein contain at least one zwitterionic surfactant.

Additional preferred oxidative dyes as contemplated herein are exemplified in that the surfactant they contain is selected from nonionic surfactants and anionic surfactants as well as mixtures thereof.

Zwitterionic surfactants refer to those surface-active compounds having at least one quaternary ammonium group and at least one carboxylate group, sulfonate group or sulfate group in the molecule. Especially suitable zwitterionic surfactants include the so-called betaines, such as N-alkyl-N,N-dimethylammonium glycinate, for example, coconut alkyldimethylammonium glycinate, N-acylaminopropyl-N,N-dimethylammonium glycinates, for example, coco acylaminopropyldimethylammonium glycinate and 2-alkyl-3-carboxymethyl-3-hydroxyethylimidazolines each with 8 to 18 carbon atoms in the alkyl group or the acyl group as well as coconut acylaminoethylhydroxyethylcarboxymethyl glycinate. A preferred zwitterionic surfactant is the fatty acid amide derivative known by the INCI designation cocamidopropyl betaine.

Amphoteric surfactants are understood to be surface-active compounds containing, in addition to a $C_8$-$C_{24}$ alkyl group or acyl group in the molecule, at least one free amino group and at least one —COOH or —SO$_3$H group and those capable of forming internal salts. Examples of suitable amphoteric surfactants include N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids, each with approximately from 8 to 24 carbon atoms in the alkyl group. Especially preferred amphoteric surfactants include N-cocoalkylaminopropionate, cocoacylaminoethylaminopropionate and $C_{12}$-$C_{18}$ acylsarcosine. Suitable anionic surfactants include all the anionic surfactant substances that are suitable for use on the human body and have a water-solubilizing anionic group, for example, a carboxylate, sulfate, sulfonate or phosphate group and a lipophilic alkyl group with approximately from 8 to 30 carbon atoms, preferably from 8 to 24 carbon atoms in the molecule. In addition, glycol groups or polyglycol ether groups, ester groups, ether groups and amide groups as well as hydroxyl groups may also be present in the molecule. Examples of suitable anionic surfactants include linear and branched fatty acids with from 8 to 30 carbon atoms (soaps), each in the form of sodium, potassium and ammonium salts as well as the mono-, di- and trialkanolammonium salts with from 2 to 4 carbon atoms in the alkanol group, polyethoxylated ether carboxylic acids, acyl sarcosides, acyl taurides, acyl isethionates, sulfosuccinic acid mono- and dialkyl esters and sulfosuccinic acid monoalkylpolyoxyethyl esters with from 1 to 6 ethylene oxide groups, linear alkane sulfonates, linear α-olefin sulfonates, sulfonates of unsaturated fatty acids with up to six double bond, α-sulfo fatty acid methyl esters of fatty acids, $C_8$-$C_{20}$ alkyl sulfates and $C_8$-$C_{20}$ alkyl ether sulfates with up to 15 ethoxide groups, mixtures of surfactant hydroxysulfonates, sulfated hydroxyalkyl polyethylene glycol ethers and/or hydroxyalkylene propylene glycol ethers, esters of tartaric acid or citric acid with ethoxylated or propoxylated fatty alcohols, optionally polyethoxylated alkyl and/or alkenyl ether phosphates, sulfated fatty acid alkylene glycol esters as well as monoglyceride sulfates and monoglyceride ether sulfates. Preferred anionic surfactants include the soaps, $C_8$-$C_{20}$ alkyl sulfates, $C_8$-$C_{20}$ alkyl ether sulfates and $C_8$-$C_{20}$ ether carboxylic acids with from 8 to 20 carbon atoms in the alkyl group and up to 12 ethylene oxide groups in the molecule. Sodium cetearyl sulfate is especially preferred.

Nonionic surfactants that are especially preferred for use are selected from castor oil ethoxylated with from about 20 to about 100 mol ethylene oxide per mol, ethoxylated $C_8$-$C_{24}$ alkanols with from about 10 to about 100 mol ethylene oxide per mol, ethoxylated $C_8$-$C_{24}$ carboxylic acids with from about 10 to about 100 mol ethylene oxide per mol, sorbitan monoesters of linear saturated and unsaturated $C_{12}$-$C_{30}$ carboxylic acids, which may be hydroxylated with from about 20 to about 100 ethylene oxide per mol ethoxylated castor oil, sorbitan monoesters ethoxylated with from about 20 to about 100 mol ethylene oxide per mol, in articular those of myristic acid, palmitic acid, stearic acid or mixtures of these fatty acids, alkyl mono- and oligoglycosides with from 8 to 22 carbon atoms in the alkyl radical and their ethoxylated analogs as well as mixtures of the aforementioned substances.

The ethoxylated $C_8$-$C_{24}$ alkanols have the formula $R^1O(CH_2CH_2O)_nH$, where $R^1$ stands for a linear or branched alkyl and/or alkenyl radical with 8-24 carbon atoms, and n stands for the average number of ethylene oxide units per molecule, from about 10 to about 100, preferably from about 10 to about 30, especially preferably from about 15 to about 25 mol ethylene oxide onto 1 mol capryl alcohol, 2-ethylhexyl alcohol, capric alcohol, lauryl alcohol, isotridecyl alcohol, myristyl alcohol, cetyl alcohol, palmitoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol and brassidyl alcohol as well as their technical grade mixtures. Adducts of from about 10-about 100 mol ethylene oxide onto technical grade fatty alcohols with from 12-18 carbon atoms, such as, for example, coconut, palm, palm kernel or tallow fatty alcohols. Especially preferred examples include laureth-10, laureth-12, laureth-15, laureth-20, laureth-30, myreth-10, myreth-12, myreth-15, myreth-20, myreth-30, ceteth-10, ceteth-12, ceteth-15, ceteth-20, ceteth-30, steareth-10, steareth-12 steareth-15, steareth-20, steareth-30, oleth-10, oleth-12, oleth-15, oleth-20, oleth-30, ceteareth-10, ceteareth-15, ceteareth-12, ceteareth-15, ceteareth-20, ceteareth-30 as well as coceth-10, coceth-12, coceth-15, coceth-20 and coceth-30.

The ethoxylated $C_8$-$C_{24}$ carboxylic acids have the formula $R^1O(CH_2CH_2O)_nH$, where $R^1O$ stands for a linear or branched, saturated or unsaturated acyl radical with from 8-24 carbon atoms and n stands for the average number of ethylene oxide units per molecule, for numbers from about 10 to about 100, preferably from about 10 to about 30 mol ethylene oxide onto 1 mol caprylic acid, 2-ethylhexanoic acid, capric acid, lauric acid, isotridecanoic acid, myristic acid, cetylic acid, palmitoleic acid, stearic acid, isostearic acid, oleic acid, elaidic acid, petroselinic acid, arachidic acid, gadoleinic acid, behenic acid, erucaic acid and brassidic acid as well as the technical grade mixtures thereof. Adducts of from about 10 to about 100 mol ethylene oxide onto technical grade fatty acids with from 12-18 carbon atoms such as coconut, palm, palm kernel or tallow fatty acid are also suitable. Especially preferred are PEG-50 monostearate, PEG-100 monostearate, PEG-50 monooleate, PEG-100 monooleate, PEG-50 monolaurate and PEG-100 monolaurate.

Preferred sorbitan monoesters, ethoxylated with from about 20- about 100 mol ethylene oxide, of linear saturated and unsaturated $C_{12}$-$C_{30}$ carboxylic acids, which may be hydroxylated, are selected from polysorbate-20, polysorbate-40, polysorbate-60 and polysorbate-80.

In addition, $C_8$-$C_{22}$ alkyl mono- and oligoglycosides are preferred. $C_8$-$C_{22}$ alkyl-mono- and oligoglycosides are known commercial surfactants and emulsifiers. They are produced by reacting glucose of oligosaccharides with primary alcohols having from 8 to 22 carbon atoms in particular. With respect to the glycoside radical, it is true that both monoglycosides in which a cyclic sugar radical is glycosidically bound to the fatty alcohol as well as oligomeric glycosides with a degree of oligomerization of up to approximately 8 preferably 1-2 are suitable. The degree of oligomerization is a statistical mean based on a standard homolog distribution for such technical-grade products. Products available under the brand name Plantacare® contain a glucosidically-bound $C_8$-$C_{16}$ alkyl group on an oligoglucoside radical whose average degree of oligomerization is 1-2, in particular 1.2-1.4. Particularly preferred $C_8$-$C_{22}$ alkyl mono- and oligoglycosides are selected from octyl glucoside, decyl glucoside, lauryl glucoside, palmityl glucoside, isostearyl glucoside, stearyl glucoside, arachidyl glucoside and behenyl glucoside as well as mixtures thereof. The acyl glucamides derived from glucamine are also suitable as nonionic oil-in-water emulsifiers.

The total amount of at least one surfactant in the oxidative dyes as contemplated herein is preferably from about 0.1 to about 20 wt %, preferably from about 0.5 to about 10 wt % and especially preferably from about 0.8 to about 4 wt %, each based on the weight of the oxidative dye.

In another preferred embodiment, the oxidative dye as contemplated herein contains a total of from about 0.1 to about 30 wt %, preferably from about 0.5 to about 20 wt % and especially preferably from about 1 to about 10 wt %, each based on the weight of the oxidative dye, a mixture of nonionic and anionic surfactants.

Additional preferred oxidative dyes as contemplated herein are exemplified in that they contain at least one linear saturated alkanol with from 12 to 30 carbon atoms.

Preferred linear saturated alkanols with from 12 to 30 carbon atoms, in particular with from 16 to 22 carbon atoms are selected from cetyl alcohol, stearyl alcohol, arachidyl alcohol, behenyl alcohol and lanolin alcohol as well as mixtures of these alkanols. Alkanol mixtures that are especially preferred as contemplated herein include those that can be obtained in technical-grade hydrogenation of vegetable and animal fatty acids. The total amount of at least one linear saturated alkanol with from 12 to 30 carbon atoms of the oxidative dyes as contemplated herein preferably amounts to from about 0.1 to about 20 wt %, preferably from about 0.5 to about 16.5 wt % and especially preferably from about 3 to about 10 wt %, each based on the weight of the oxidative dye.

The oxidative dye as contemplated herein contains at least one oxidative dye precursor of the developer type and at least one oxidative dye precursor of the coupler type as obligatory ingredients.

Oxidative dye precursors can be divided into two categories based on their reaction behavior, namely so-called developer components and coupler components.

Coupler components alone do not develop a significant coloration within the context of oxidative dyeing but always require the presence of developer components. Developer components can form the actual coloring substance per se.

The developer and coupler components are usually used in free form. However, in the case of substances with amino groups, it may be preferable to use them in salt form, in particular in the form of the hydrochlorides or hydrobromides or sulfates.

Especially preferred developer components are selected from at least one compound from the group formed from p-phenylenediamine, p-toluylenediamine, 2-(2-hydroxyethyl)-p-phenylenediamine, 2-(1,2-dihydroxyethyl)-p-phenylenediamine, N,N-bis-(2-hydroxyethyl)-p-phenylenediamine, 2-methoxymethyl-p-phenylenediamine, N-(4-amino-3-methylphenyl)-N-[3-(1H-imidazol-1-yl) propyl]amine, N,N'-bis-(2-hydroxyethyl)-N,N'-bis-(4-aminophenyl)-1,3-diaminopropan-2-ol, bis-(2-hydroxy-5-aminophenyl)methane, 1,3-bis-(2,5-diaminophenoxy)propan-2-ol, N,N'-bis-(4-aminophenyl)-1,4-diazacycloheptane, 1,10-bis-(2,5-diaminophenyl)-1,4,7,10-tetraoxadecane, p-aminophenol, 4-amino-3-methylphenol, 4-amino-2-aminomethylphenol, 4-amino-2-(1,2-dihydroxyethyl)phenol and 4-amino-2-(diethylaminomethyl)phenol, 4,5-diamino-1-(2-hydroxyethyl) pyrazole, 2,4,5,6-tetraaminopyrimidine, 4-hydroxy-2,5,6-triaminopyrimidine, 2-hydroxy-4,5,6-triaminopyrimidine, the physiologically tolerable salts of these compounds as well as mixtures of these developer components and developer component salts.

Most especially preferred developer components are selected from 4,5-diamino-1-(2-hydroxyethyl)pyrazole, p-toluylenediamine, 2-(2-hydroxyethyl)-p-phenylenediamine, 2-methoxymethyl-p-phenylenediamine, N-(4-amino-3-methylphenyl)-N-[3-(1H-imidazol-1-yl)propyl]amine and mixtures of these compounds as well as their physiologically tolerable salts. An extremely preferred component is 4,5-diamino-1-(2-hydroxyethyl)pyrazole and its physiologically tolerable salts.

Preferably at least one developer component is present in a total amount of from about 0.01 to about 5 wt %, preferably from about 0.1 to about 4 wt %, especially preferably from about 0.2 to about 2.5 wt %, each based on the weight of the oxidative dye as contemplated herein.

Preferably at least one coupler component is present in a total amount of from about 0.001 to about 4 wt %, preferably from about 0.01 to about 2 wt %, especially preferably from about 0.05 to about 1 wt %, extremely preferably from about 0.1 to about 0.5 wt %, each based on the weight of the oxidative dye as contemplated herein.

The term "ready-to-use dye" is understood in the sense of this patent application to refer to a mixture of all the oxidative dye precursors and all the oxidizing agents, optionally in combination with a suitable cosmetic vehicle, for example, a cream base and optionally in combination with at least one direct dye.

Coupler components as contemplated herein allow at least one substitution of a chemical radical of the coupler by the oxidized form of the developer component, in which a covalent bond is formed between the coupler component and the developer component. Couplers are preferably cyclic compounds having at least two groups on the ring, selected from (i) optionally substituted amino groups and/or (ii) hydroxyl groups. If the cyclic compound is a six-membered ring (preferably aromatic), then said groups are preferably in ortho-position or meta-position to one another.

Preferred agents as contemplated herein are exemplified in that the at least one oxidative dye precursor of the coupler type is selected from one of the following classes:
3-aminophenol (m-aminophenol) and/or derivatives thereof,
3-aminoaniline (m-diaminobenzene) and/or derivatives thereof,
2-aminoaniline (1,2-diaminobenzene; o-diaminobenzene) and/or derivatives thereof,
2-aminophenol (o-aminophenol) and/or derivatives thereof,
naphthalene derivatives having at least one hydroxyl group,
di- or trihydroxybenzene and/or derivatives thereof,
pyridine derivatives,
pyrimidine derivatives,
monohydroxyindole derivatives and/or monoaminoindole derivatives,
monohydroxyindoline derivatives and/or monoaminoindoline derivatives,
pyrazolone derivatives such as 1-phenyl-3-methylpyrazol-5-one, for example,
morpholine derivatives such as 6-hydroxybenzomorpholine or 6-aminobenzomorpholine, for example,
quinoxaline derivatives such as 6-methyl-1,2,3,4-tetrahydroquinoxaline, for example.

Mixtures of two or more compounds from one or more of these classes are also preferred as contemplated herein within the scope of this specific embodiment.

Particularly preferred additional coupler components as contemplated herein are selected from 3-aminophenol, 5-amino-2-methylphenol, 3-amino-2-chloro-6-methylphenol, 2-hydroxy-4-aminophenoxy ethanol, 5-amino-4-chloro-2-methylphenol, 5-(2-hydroxyethyl)amino-2-methylphenol, 2,4-dichloro-3-aminophenol, 2-aminophenol, 3-phenylenediamine, 2-(2,4-diaminophenoxy)ethanol, 1,3-bis(2,4-diaminophenoxy)propane, 1-methoxy-2-amino-4-(2'-hydroxy ethylamino)benzene (=2-amino-4-hydroxyethylaminoanisole), 1,3-bis(2,4-diaminophenyl)propane, 2,6-bis(2'-hydroxyethylamino)-1-methylbenzene, 2-({3-[(2-hydroxyethyl)amino]-4-methoxy-5-methyphenyl}amino)ethanol, 2-({3-[(2-hydroxyethyl)amino]-2-methoxy-5-methylphenyl}amino)ethanol, 2-({3-[(2-hydroxyethyl)amino]-4,5-dimethylphenyl}amino)ethanol, 2-[3-morpholin-4-ylphenyl)amino]ethanol, 3-amino-4-(2-methoxyethoxy)-5-methylphenylamine, 1-amino-3-bis-(2-hydroxyethyl)aminobenzene, resorcinol, 2-methylresorcinol, 4-chlororesorcinol, 1,2,4-trihydroxybenzene, 2-amino-3-hydroxypyridine, 3-amino-2-methylamino-6-methoxypyridine, 2,6-dihydroxy-3,4-dimethylpyridine, 3,5-diamino-2,6-dimethoxypyridine, 1-phenyl-3-methylpyrazol-5-one, 1-naphthol, 1,5-dihydroxynaphthalene, 2,7-dihydroxynaphthalene, 1,7-dihydroxynaphthalene, 1,8-dihydroxynaphthalene, 4-hydroxyindole, 6-hydroxyindole, 7-hydroxyindole, 4-hydroxyindoline, 6-hydroxyindoline, 7-hydroxyindoline or mixtures of these compounds or the physiologically tolerable salts of the aforementioned compounds.

Most especially preferred here are 3-aminophenol, resorcinol, 2-methylresorcinol, 5-amino-2-methylphenol, 2-(2,4-diaminophenoxy)ethanol, 1,3-bis(2,4-diaminophenoxy)propane, 1-methoxy-2-amino-4-(2'-hydroxyethylamino) benzene, 2-amino-3-hydroxypyridine and 1-naphthol as well as their physiologically tolerable salts and mixtures of the aforementioned components.

The at least one coupler component is preferably present in a total amount of from about 0.01 to about 20 wt %, especially preferably from about 0.2 to about 10 wt % and extremely preferably from about 0.6 to about 5 wt %, each based on the weight of the oxidative dye as contemplated herein.

Within the scope of the present disclosure, the following combinations of oxidative dye precursors of the developer type and of the coupler type are especially preferred, wherein the amine compounds and the nitrogen heterocycles may also be present in the form of their physiologically tolerable salts:

p-Toluylenediamine/resorcinol;
p-Toluylenediamine/2-methylresorcinol;
p-Toluylenediamine/5-amino-2-methylphenol;
p-Toluylenediamine/3-aminophenol;
p-Toluylenediamine/2-(2,4-diaminophenoxy)ethanol;
p-Toluylenediamine/1,3-bis(2,4-diaminophenoxy)propane;
p-Toluylenediamine/1-methoxy-2-amino-4-(2-hydroxyethylamino)benzene;
p-Toluylenediamine/2-amino-3-hydroxypyridine;
p-Toluylenediamine/1-naphthol;
2-(2-Hydroxyethyl)-p-phenylenediamine/resorcinol;
2-(2-Hydroxyethyl)-p-phenylenediamine/2-methylresorcinol;
2-(2-Hydroxyethyl)-p-phenylenediamine/5-amino-2-methylphenol;
2-(2-Hydroxyethyl)-p-phenylenediamine/3-aminophenol;
2-(2-Hydroxyethyl)-p-phenylenediamine/2-(2,4-diaminophenoxy)ethanol;
2-(2-Hydroxyethyl)-p-phenylenediamine/1,3-bis(2,4-diaminophenoxy)propane;
2-(2-Hydroxyethyl)-p-phenylenediamine/1-methoxy-2-amino-4-(2-hydroxyethylamino)benzene;
2-(2-Hydroxyethyl)-p-phenylenediamine/2-amino-3-hydroxypyridine;
2-(2-Hydroxyethyl)-p-phenylenediamine/1-naphthol;
2-Methoxymethyl-p-phenylenediamine/resorcinol;
2-Methoxymethyl-p-phenylenediamine/2-methylresorcinol;
2-Methoxymethyl-p-phenylenediamine/5-amino-2-methylphenol;
2-Methoxymethyl-p-phenylenediamine/3-aminophenol;
2-Methoxymethyl-p-phenylenediamine/2-(2,4-diaminophenoxy)ethanol;
2-Methoxymethyl-p-phenylenediamine/1,3-bis(2,4-diaminophenoxy)propane;
2-Methoxymethyl-p-phenylenediamine/1-methoxy-2-amino-4-(2-hydroxyethylamino)benzene;
2-Methoxymethyl-p-phenylenediamine/2-amino-3-hydroxypyridine;
2-Methoxymethyl-p-phenylenediamine/1-naphthol;
N-(4-Amino-3-methylphenyl)-N-[3-(1H-imidazol-1-yl)propyl]amine/resorcinol;
N-(4-Amino-3-methylphenyl)-N-[3-(1H-imidazol-1-yl)propyl]amine/2-methylresorcinol;
N-(4-Amino-3-methylphenyl)-N-[3-(1H-imidazol-1-yl)propyl]amine 5-amino-2-methylphenol;
N-(4-Amino-3-methylphenyl)-N-[3-(1H-imidazol-1-yl)propyl]amine/3-aminophenol;
N-(4-Amino-3-methylphenyl)-N-[3-(1H-imidazol-1-yl)propyl]amine 2-(2,4-diaminophenoxy)ethanol;
N-(4-Amino-3-methylphenyl)-N-[3-(1H-imidazol-1-yl)propyl]amine/1,3-bis(2,4-diaminophenoxy)propane;
N-(4-Amino-3-methylphenyl)-N-[3-(1H-imidazol-1-yl)propyl]amine/1-methoxy-2-amino-4-(2-hydroxyethylamino)benzene;
N-(4-Amino-3-methylphenyl)-N-[3-(1H-imidazol-1-yl)propyl]amine/2-amino-3-hydroxypyridine;
N-(4-Amino-3-methylphenyl)-N-[3-(1H-imidazol-1-yl)propyl]amine/1-naphthol;
4,5-Diamino-1-(2-hydroxyethyl)pyrazole/resorcinol;
4,5-Diamino-1-(2-hydroxyethyl)pyrazole/2-methylresorcinol;
4,5-Diamino-1-(2-hydroxyethyl)pyrazole/5-amino-2-methylphenol;
4,5-Diamino-1-(2-hydroxyethyl)pyrazole/3-aminophenol;
4,5-Diamino-1-(2-hydroxyethyl)pyrazole/2-(2,4-diaminophenoxy)ethanol;
4,5-Diamino-1-(2-hydroxyethyl)pyrazole/1,3-bis(2,4-diaminophenoxy)propane;
4,5-Diamino-1-(2-hydroxyethyl)pyrazole/1-methoxy-2-amino-4-(2-hydroxyethylamino)benzene;
4,5-Diamino-1-(2-hydroxyethyl)pyrazole/2-amino-3-hydroxypyridine;
4,5-Diamino-1-(2-hydroxyethyl)pyrazole/1-naphthol.

Especially preferred as contemplated herein are the combinations of 4,5-diamino-1-(2-hydroxyethyl)pyrazole/3-aminophenol and p-toluylenediamine/3-aminophenol. The combination 4,5-diamino-1-(2-hydroxyethyl)pyrazole/3-aminophenol is extremely preferred, in particular with regard to the improvement in washfastness.

To achieve a balanced and subtle development of a nuance, it is preferable as contemplated herein if additional color-imparting components are contained in the oxidative dye as contemplated herein.

In another embodiment, the oxidative dyes as contemplated herein may additionally contain at least one direct dye. These are dyes which are absorbed directly by the hair and do not require any oxidative process to form the color. Direct dyes are usually nitrophenylenediamines, nitroaminophenols, azo dyes, anthraquinones or indophenols.

The oxidative dyes as contemplated herein may contain additional ingredients. It is preferable here to use polyvalent alcohols which have moisture distributing properties. Oxidative dyes as contemplated herein containing at least one polyvalent alcohol, preferably selected from the group comprising sorbitol and/or glycerol and/or 1,2-propylene glycol or mixtures thereof in a total amount of from about 0.05 to about 15 wt %, preferably from about 0.1 to about 10 wt %, especially preferably from about 0.15 to about 5 wt % and in particular from about 0.15 to about 1 wt %, each based on the weight of the oxidative dye. For certain application areas it may be advantageous to use only one of the three preferred polyvalent alcohols mentioned above. In most cases, glycerol is preferred here. However, mixtures of two of the three polyvalent alcohols or all three polyvalent alcohols may be preferred in other fields of application. A mixture of glycerol, sorbitol and 1,2-propylene glycol in a weight ratio of 1:(from about 0.5 to about 1):(from about 0.1 to about 0.5) has proven to be particularly advantageous here. In addition to sorbitol, glycerol and 1,2-propylene glycol, other polyvalent alcohols that are suitable includes those having at least two OH groups, preferably mannitol, xylitol, polyethylene glycol, polypropylene glycol and mixtures thereof. Of these compounds those with from 2 to 12 OH groups and in particular those with 2, 3, 4, 5, 6 or 10 OH groups are preferred.

The oxidative dye as contemplated herein is mixed with an oxidizing agent preparation (B) to form a ready-to-use agent containing at least one oxidizing agent. Preferred oxidizing agents are selected from peroxo compounds, preferably selected from hydrogen peroxide, solid addition compounds of hydrogen peroxide onto organic or inorganic compounds, such as sodium perborate, sodium percarbonate, magnesium percarbonate, sodium percarbamide, polyvinyl pyrrolidone·$nH_2O_2$ (n is a positive integer greater than 0), urea peroxide and melamine peroxide, also selected from diammonium peroxodisulfate (also known as ammonium persulfate), disodium peroxodisulfate (also known as sodium persulfate) and dipotassium peroxodisulfate (also known as potassium persulfate) as well as mixtures of these oxidizing agents. Oxidizing agents that are most especially preferred for use as contemplated herein are aqueous hydrogen peroxide solutions. The concentration of a hydrogen peroxide solution is determined, on the one hand, by the statutory specifications and, on the other hand, by the desired effect, preferably using from about 6 wt % to about 12 wt % solutions in water. Oxidative dyes that are preferred as contemplated herein are exemplified in that the composition (B) used to prepare them contains—based on its weight—from about 1 to about 24 wt %, preferably from about 4 to about 10 wt %, especially preferably from about 3 to about 6 wt % hydrogen peroxide (calculated as 100% $H_2O_2$).

For oxidative hair dye methods the contemplated dye which contains one or more oxidative dye precursors and optionally one or more direct dyes is mixed with an aqueous composition (B) containing an oxidizing agent, usually shortly before application to the hair, to form the ready-to-use agent which is then applied to the hair. In most cases the contemplated dye (A) and the composition (B) containing the oxidizing agent are coordinated with one another so that an initial concentration of hydrogen peroxide of from about 0.5 to about 12 wt %, preferably from about 2 to about 10 wt %, especially preferably from about 3 to about 6 wt % hydrogen peroxide (calculated as 100% $H_2O_2$) based on the weight of the oxidative dye is obtained at a mixing ratio of from about 1 to 1, based on parts by weight, in the hair dye product. However, it is equally possible to coordinate the dye (A) as contemplated herein and the composition (B) containing the oxidizing agent with one another so that the concentrations required in the ready-to-use oxidative dye are obtained with mixing ratios other than 1:1, for example, by a weight-based mixing ratio of 1:2 or 1:3 or even 2:3.

For a dyeing which requires a great lightening of very dark hair, the use of hydrogen peroxide or addition products thereof onto organic and/or inorganic compounds is often inadequate. In these cases a combination of hydrogen peroxide and peroxodisulfate salts (persulfate salts) is generally used. Preferred persulfate salts include ammonium peroxodisulfate, potassium peroxodisulfate, sodium peroxodisulfate as well as mixtures thereof.

The at least one persulfate salt is preferably present in a total amount of from about 0.1 to about 25 wt %, especially preferably in a total amount of from about 1 to about 15 wt %, based on the weight of the oxidative dye as contemplated herein.

Another subject matter of the present patent application is a kit for dyeing and/or lightening keratinic fibers, comprising an agent as described above and an oxidizing agent preparation.

With regard to additional preferred embodiments of the kit as contemplated herein, what was said about the agents as contemplated herein and the oxidizing agent preparations used as contemplated herein also holds here, mutatis mutandis.

Another subject matter of the present patent application is a method for dyeing and/or lightening keratinic fibers comprising the following process steps:

optionally applying a pretreatment agent M1 to the fibers, then mixing the contemplated agent M2 as described above with an oxidizing agent preparation and applying the preparation to the fibers, rinsing out the fibers after a period of from about 1 to about 60 minutes, and then optionally applying an after-treatment agent M3 to the fibers and rinsing it off after a treatment time of from about 0.5 to about 30 minutes.

With respect to additional preferred embodiments of the method as contemplated herein, what was said about regarding the agents as contemplated herein and the oxidizing agent preparations to be used also holds here, mutatis mutandis.

EXAMPLE

TABLE 1

The following dyes and/or compositions (A) were prepared (oil-in-water emulsions, all amounts in wt %):

| Raw material | Comparative 1 | E1* | E2* |
| --- | --- | --- | --- |
| Xanthan gum | 0.1 | 0.1 | 0.1 |
| 2-Octyldodecanol | 2.3 | 2.3 | 2.3 |
| Cetearyl alcohol | 18.0 | 18.0 | 18.0 |
| Glycerol monostearate | 6.0 | 6.0 | 6.0 |
| Glycerol 99.5% | 2.0 | 2.0 | 2.0 |
| Cocoamidopropylbetaine | 0.8 | 0.8 | 0.8 |
| Monoethanolamine | 6.0 | 6.0 | 6.0 |
| 2-Amino-2-methylpropanol | 0.10 | 0.10 | 0.10 |
| Sodium sulfite, anhydrous | 0.30 | 0.30 | 0.30 |
| Caramel syrup 75% | 0.10 | 0.10 | 0.10 |
| Ascorbic acid | 0.10 | 0.10 | 0.10 |
| Grapeseed oil | 1.0 | 1.0 | 1.0 |
| p-Toluylenediaminesulfate | 0.10 | 0.10 | 0.10 |
| Resorcinol | 0.02 | 0.02 | 0.02 |
| m-Aminophenol | 0.003 | 0.003 | 0.003 |
| 4-Chlororesorcinol | 0.03 | 0.03 | 0.03 |
| Ingredients extracted from bark-free Quassia amara-wood with water | — | 0.15 | 0.3 |
| Water deionized | to Σ 100 | to Σ 100 | to Σ 100 |

*as contemplated in the present disclosure

The fat base was melted together at 80° C. and dispersed in a small amount of the water. Next the remaining ingredients of the formulation were incorporated in order while stirring. Then the mixture was topped off with water to 100 wt % and the formulation was stirred cold. Recipe V1 is a comparative formulation that does not contain Quassia amara extract and is not as contemplated herein. Recipes E1 and E2 are as contemplated in the present disclosure.

TABLE 2

| Oxidizing agent preparation (B) (all amounts in wt %) | |
| --- | --- |
| Raw material | (B) |
| Disodium pyrophosphate | 0.10 |
| Dipicolinic acid | 0.10 |
| Potassium hydroxide 50% | 0.30 |
| 1-Hydroxyethane-1,1-diphosphonic acid 60% | 0.25 |
| Fatty alcohol sulfate $C_{16}$-$C_{18}$ sodium salt | 0.30 |
| PEG-40 castor oil | 0.60 |
| Cetearyl alcohol | 3.6 |
| Ceteareth-20 | 0.50 |
| Beeswax | 0.30 |
| Isopropyl myristate | 10.0 |
| Hydrogen peroxide | 11.6 |
| Water deionized | to 100 |

2. Stronger Lightening (L Value) Due to the Addition of the Quassia Amara Extract To prepare the oxidative dye for determining the color shift, the cosmetic agents V1, E2 and E1 were each mixed with the above oxidizing agent preparation (B) in a weight ratio of 1:2.

The oxidative dyes prepared in this way were each applied to strands of yak hair in a defined amount (4 g oxidative dye per 1 g yak hair) (12 strands of hair each per oxidative dye) and remained on the strands of hair for a treatment time of 30 minutes at 32° C. Next, the remaining agents were each rinse out of the strands of hair for 2 minutes using lukewarm water, the strands were first dried with a towel and then blow dried.

All the strands were measured using a colorimeter model Spectraflash 450 from the company Datacolor. The L* color value, measured on the respective strands was used for the evaluation of lightening. The higher the value for L, the greater is the lightening of the strands.

The following table shows the L values for the dyeings using the dyes E1 and E2 as contemplated herein in comparison with V1. The dyeings using the cosmetic agents E1 and E2 as contemplated herein, containing 0.15 wt % and 0.3 wt %, ingredients extracted from bark-free Quassia amara wood using water have a stronger lightening effect (L=71.0 and 71.3) than the similar dye without the Quassia amara extract.

TABLE 3

| L values for dyeings using the dyes E1 and E2 as contemplated in the present disclosure in comparison with V1 | |
| --- | --- |
| Oxidative dye mixture | L value |
| E1 + O1 (1:2) 2% (0.15%) QA | 71.0 |
| E2 + O1 (1:2) 4% (0.3%) QA | 71.3 |
| V2 + O1 (1:2) 0% QA | 66.3 |

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. An oxidative dye for oxidative color change of keratinic fibers, comprising, in a cosmetically suitable vehicle, at least one alkalizing agent, at least one oxidative dye precursor of the developer type and at least one oxidative dye precursor of the coupler type, at least one extract of Quassia amara and from about 0 to less than about 0.1 wt % of peroxide compounds, based on the weight of the oxidative dye.

2. The oxidative dye according to claim 1, comprising the at least one extract of Quassia amara amounting to a total of from about 0.01 to about 3 wt %, based on the weight of the oxidative dye.

3. The oxidative dye according to claim 1, wherein the extract is obtained from the wood of Quassia amara.

4. The oxidative dye according to claim 1, comprising at least one cosmetic oil.

5. The oxidative dye according to claim 4, wherein the at least one cosmetic oil is included in a total amount of from about 0.1 to about 80 wt %, based on the weight of the oxidative dye.

6. The oxidative dye according to claim 1, comprising at least one surfactant.

7. The oxidative dye according to claim 1, comprising at least one surfactant in a total amount of from about 0.1 to about 30 wt %, based on the weight of the oxidative dye.

8. The oxidative dye according to claim 1, comprising at least one linear saturated alkanol with from 12 to 30 carbon atoms.

9. The oxidative dye according to claim 1, comprising at least one linear saturated alkanol with from 12 to 30 carbon atoms in a total amount of from about 0.1 to about 20 wt %, based on the weight of the oxidative dye.

10. The oxidative dye according to claim 1, comprising a combination of at least one oxidative dye precursor of the developer type and at least one oxidative dye precursor of the coupler type which is selected from at least one of the following combinations, wherein the amine compounds and the nitrogen heterocycles may also be present in the form of their physiologically tolerable salts:
  p-Toluylenediamine/resorcinol;
  p-Toluylenediamine/2-methylresorcinol;
  p-Toluylenediamine/5-amino-2-methylphenol;
  p-Toluylenediamine/3-aminophenol;
  p-Toluylenediamine/2-(2,4-diaminophenoxy)ethanol;
  p-Toluylenediamine/1,3-bis(2,4-diaminophenoxy)propane;
  p-Toluylenediamine/1-methoxy-2-amino-4-(2-hydroxyethylamino)benzene;
  p-Toluylenediamine/2-amino-3-hydroxypyridine;
  p-Toluylenediamine/1-naphthol;
  2-(2-Hydroxyethyl)-p-phenylenediamine/resorcinol;
  2-(2-Hydroxyethyl)-p-phenylenediamine/2-methylresorcinol;
  2-(2-Hydroxyethyl)-p-phenylenediamine/5-amino-2-methylphenol;
  2-(2-Hydroxyethyl)-p-phenylenediamine/3-aminophenol;
  2-(2-Hydroxyethyl)-p-phenylenediamine/2-(2,4-diaminophenoxy)ethanol;
  2-(2-Hydroxyethyl)-p-phenylenediamine/1,3-bis(2,4-diaminophenoxy)propane;
  2-(2-Hydroxyethyl)-p-phenylenediamine 1-methoxy-2-amino-4-(2-hydroxyethylamino)benzene;
  2-(2-Hydroxyethyl)-p-phenylenediamine/2-amino-3-hydroxypyridine;
  2-(2-Hydroxyethyl)-p-phenylenediamine/1-naphthol;

2-Methoxymethyl-p-phenylenediamine/resorcinol;
2-Methoxymethyl-p-phenylenediamine/2-methylresorcinol;
2-Methoxymethyl-p-phenylenediamine/5-amino-2-methylphenol;
2-Methoxymethyl-p-phenylenediamine/3-aminophenol;
2-Methoxymethyl-p-phenylenediamine/2-(2,4-diaminophenoxy)ethanol;
2-Methoxymethyl-p-phenylenediamine/1,3-bis(2,4-diaminophenoxy)propane;
2-Methoxymethyl-p-phenylenediamine/1-methoxy-2-amino-4-(2-hydroxyethylamino)-benzene;
2-Methoxymethyl-p-phenylenediamine/2-amino-3-hydroxypyridine;
2-Methoxymethyl-p-phenylenediamine/1-naphthol;
N-(4-Amino-3-methylphenyl)-N-[3-(1H-imidazol-1-yl)propyl]amine/resorcinol;
N-(4-Amino-3-methylphenyl)-N-[3-(1H-imidazol-1-yl)propyl]amine 2-methylresorcinol;
N-(4-Amino-3-methylphenyl)-N-[3-(1H-imidazol-1-yl)propyl]amine/5-amino-2-methylphenol;
N-(4-Amino-3-methylphenyl)-N-[3-(1H-imidazol-1-yl)propyl]amine/3-aminophenol;
N-(4-Amino-3-methylphenyl)-N-[3-(1H-imidazol-1-yl)propyl]amine/2-(2,4-diamino-phenoxy)ethanol;
N-(4-Amino-3-methylphenyl)-N-[3-(1H-imidazol-1-yl)propyl]amine/1,3-bis(2,4-diaminophenoxy)propane;
N-(4-Amino-3-methylphenyl)-N-[3-(1H-imidazol-1-yl)propyl]amine/1-methoxy-2-amino-4-(2-hydroxyethylamino)benzene;
N-(4-Amino-3-methylphenyl)-N-[3-(1H-imidazol-1-yl)propyl]amine/2-amino-3-hydroxypyridine;
N-(4-Amino-3-methylphenyl)-N-[3-(1H-imidazol-1-yl)propyl]amine/1-naphthol;
4,5-Diamino-1-(2-hydroxyethyl)pyrazole/resorcinol;
4,5-Diamino-1-(2-hydroxyethyl)pyrazole/2-methylresorcinol;
4,5-Diamino-1-(2-hydroxyethyl)pyrazole/5-amino-2-methylphenol;
4,5-Diamino-1-(2-hydroxyethyl)pyrazole/3-aminophenol;
4,5-Diamino-1-(2-hydroxyethyl)pyrazole/2-(2,4-diaminophenoxy)ethanol;
4,5-Diamino-1-(2-hydroxyethyl)pyrazole/1,3-bis(2,4-diaminophenoxy)propane;
4,5-Diamino-1-(2-hydroxyethyl)pyrazole 1-methoxy-2-amino-4-(2-hydroxyethylamino)benzene;
4,5-Diamino-1-(2-hydroxyethyl)pyrazole/2-amino-3-hydroxypyridine;
4,5-Diamino-1-(2-hydroxyethyl)pyrazole/1-naphthol.

11. The oxidative dye according to claim 2, comprising the at least one extract of Quassia amara amounting to a total of from about 0.15 to about 0.5 wt %, based on the weight of the oxidative dye.

12. The oxidative dye according to claim 4, comprising at least one cosmetic oil selected from natural and synthetic hydrocarbons; the benzoic acid esters of linear or branched $C_{8-22}$ alkanols; fatty alcohols with from 6 to 30 carbon atoms, which are unsaturated or saturated and branched or unsaturated and branched; triglycerides of linear or branched, saturated or unsaturated optionally hydroxylated $C_{8-30}$ fatty acids; the dicarboxylic acid esters of linear or branched $C_2$-$C_{10}$ alkanols; the esters of linear or branched, saturated or unsaturated fatty alcohols with from 2 to 30 carbon atoms with linear or branched, saturated or unsaturated fatty acids with from 2 to 30 carbon atoms which may be hydroxylated; the addition products of from 1 to 5 propylene oxide units onto monovalent or polyvalent $C_8$-$C_{22}$ alkanols; the addition products of at least 6 ethylene oxide units and/or propylene oxide units onto monovalent or polyvalent $C_{3-22}$ alkanols; the $C_8$-$C_{22}$ fatty alcohol esters of monovalent or polyvalent $C_2$-$C_7$ hydroxycarboxylic acids; the symmetrical, asymmetrical or cyclic esters of carbonic acid with $C_{3-22}$ alkanols, $C_{3-22}$ alkanediols or $C_{3-22}$ alkanetriols; the esters of dimers of unsaturated $C_{12}$-$C_{22}$ fatty acids (dimer fatty acids) with monovalent linear, branched or cyclic $C_2$-$C_{18}$ alkanols or with polyvalent linear or branched $C_2$-$C_6$ alkanols; silicone oils; as well as mixtures of the aforementioned substances.

13. The oxidative dye according to claim 5, wherein the at least one cosmetic oil is included in a total amount of from about 2 to about 10 wt %, based on the weight of the oxidative dye.

14. The oxidative dye according to claim 1, comprising at least one surfactant in a total amount of from about 1 to about 10 wt %, based on the weight of the oxidative dye.

15. The oxidative dye according to claim 1, comprising at least one linear saturated alkanol with from 12 to 30 carbon atoms in a total amount of from about 3 to about 10 wt %, based on the weight of the oxidative dye.

16. The oxidative dye according to claim 1, further comprising at least one cosmetic oil, at least one surfactant, and at least one linear saturated alkanol with from 12 to 30 carbon atoms.

17. An oxidative dye for oxidative color change of keratinic fibers, comprising in a cosmetically suitable vehicle:
at least one alkalizing agent,
at least one oxidative dye precursor of the developer type and at least one oxidative dye precursor of the coupler type,
at least one extract of Quassia amara amounting to a total of from about 0.15 to about 0.5 wt %, based on the weight of the oxidative dye,
from about 0 to less than about 0.1 wt % of peroxide compounds, based on the weight of the oxidative dye,
at least one cosmetic oil included in a total amount of from about 2 to about 10 wt %, based on the weight of the oxidative dye,
at least one surfactant in a total amount of from about 1 to about 10 wt %, based on the weight of the oxidative dye, and
at least one linear saturated alkanol with from 12 to 30 carbon atoms in a total amount of from about 3 to about 10 wt %, based on the weight of the oxidative dye.

18. The oxidative dye according to claim 17, comprising a combination of at least one oxidative dye precursor of the developer type and at least one oxidative dye precursor of the coupler type which is selected from at least one of the following combinations, wherein the amine compounds and the nitrogen heterocycles may also be present in the form of their physiologically tolerable salts:
p-Toluylenediamine/resorcinol;
p-Toluylenediamine/2-methylresorcinol;
p-Toluylenediamine/5-amino-2-methylphenol;
p-Toluylenediamine/3-aminophenol;
p-Toluylenediamine/2-(2,4-diaminophenoxy)ethanol;
p-Toluylenediamine/1,3-bis(2,4-diaminophenoxy)propane;
p-Toluylenediamine/1-methoxy-2-amino-4-(2-hydroxyethylamino)benzene;
p-Toluylenediamine/2-amino-3-hydroxypyridine;
p-Toluylenediamine/1-naphthol;
2-(2-Hydroxyethyl)-p-phenylenediamine/resorcinol;

2-(2-Hydroxyethyl)-p-phenylenediamine/2-methylresorcinol;
2-(2-Hydroxyethyl)-p-phenylenediamine/5-amino-2-methylphenol;
2-(2-Hydroxyethyl)-p-phenylenediamine/3-aminophenol;
2-(2-Hydroxyethyl)-p-phenylenediamine/2-(2,4-diaminophenoxy)ethanol;
2-(2-Hydroxyethyl)-p-phenylenediamine/1,3-bis(2,4-diaminophenoxy)propane;
2-(2-Hydroxyethyl)-p-phenylenediamine 1-methoxy-2-amino-4-(2-hydroxyethylamino)benzene;
2-(2-Hydroxyethyl)-p-phenylenediamine/2-amino-3-hydroxypyridine;
2-(2-Hydroxyethyl)-p-phenylenediamine/1-naphthol;
2-Methoxymethyl-p-phenylenediamine/resorcinol;
2-Methoxymethyl-p-phenylenediamine/2-methylresorcinol;
2-Methoxymethyl-p-phenylenediamine/5-amino-2-methylphenol;
2-Methoxymethyl-p-phenylenediamine/3-aminophenol;
2-Methoxymethyl-p-phenylenediamine/2-(2,4-diaminophenoxy)ethanol;
2-Methoxymethyl-p-phenylenediamine/1,3-bis(2,4-diaminophenoxy)propane;
2-Methoxymethyl-p-phenylenediamine/1-methoxy-2-amino-4-(2-hydroxyethylamino)-benzene;
2-Methoxymethyl-p-phenylenediamine/2-amino-3-hydroxypyridine;
2-Methoxymethyl-p-phenylenediamine/1-naphthol;
N-(4-Amino-3-methylphenyl)-N-[3-(1H-imidazol-1-yl)propyl]amine/resorcinol;
N-(4-Amino-3-methylphenyl)-N-[3-(1H-imidazol-1-yl)propyl]amine 2-methylresorcinol;
N-(4-Amino-3-methylphenyl)-N-[3-(1H-imidazol-1-yl)propyl]amine/5-amino-2-methylphenol;
N-(4-Amino-3-methylphenyl)-N-[3-(1H-imidazol-1-yl)propyl]amine/3-aminophenol;
N-(4-Amino-3-methylphenyl)-N-[3-(1H-imidazol-1-yl)propyl]amine/2-(2,4-diamino-phenoxy)ethanol;
N-(4-Amino-3-methylphenyl)-N-[3-(1H-imidazol-1-yl)propyl]amine/1,3-bis(2,4-diaminophenoxy)propane;
N-(4-Amino-3-methylphenyl)-N-[3-(1H-imidazol-1-yl)propyl]amine/1-methoxy-2-amino-4-(2-hydroxyethylamino)benzene;
N-(4-Amino-3-methylphenyl)-N-[3-(1H-imidazol-1-yl)propyl]amine/2-amino-3-hydroxypyridine;
N-(4-Amino-3-methylphenyl)-N-[3-(1H-imidazol-1-yl)propyl]amine/1-naphthol;
4,5-Diamino-1-(2-hydroxyethyl)pyrazole/resorcinol;
4,5-Diamino-1-(2-hydroxyethyl)pyrazole/2-methylresorcinol;
4,5-Diamino-1-(2-hydroxyethyl)pyrazole/5-amino-2-methylphenol;
4,5-Diamino-1-(2-hydroxyethyl)pyrazole/3-aminophenol;
4,5-Diamino-1-(2-hydroxyethyl)pyrazole/2-(2,4-diaminophenoxy)ethanol;
4,5-Diamino-1-(2-hydroxyethyl)pyrazole/1,3-bis(2,4-diaminophenoxy)propane;
4,5-Diamino-1-(2-hydroxyethyl)pyrazole 1-methoxy-2-amino-4-(2-hydroxyethylamino)benzene;
4,5-Diamino-1-(2-hydroxyethyl)pyrazole/2-amino-3-hydroxypyridine;
4,5-Diamino-1-(2-hydroxyethyl)pyrazole/1-naphthol.

\* \* \* \* \*